(12) United States Patent
Kim et al.

(10) Patent No.: US 12,036,090 B2
(45) Date of Patent: Jul. 16, 2024

(54) DRILL FOR DENTAL IMPLANT

(71) Applicant: TRUABUTMENT KOREA, INC., Gyeonggi-do (KR)

(72) Inventors: Haeng Oh Kim, Busan (KR); Sung Yong Kim, Seoul (KR); Hyung Ick Kim, Fullerton, CA (US); Seung Hwa Lee, Gyeonggi-do (KR)

(73) Assignee: TRUABUTMENT KOREA, INC., Gyeonggi-do (KR)

( * ) Notice: Subject to any disclaimer, the term of this patent is extended or adjusted under 35 U.S.C. 154(b) by 786 days.

(21) Appl. No.: 16/387,907

(22) Filed: Apr. 18, 2019

(65) Prior Publication Data
US 2019/0321144 A1    Oct. 24, 2019

(51) Int. Cl.
*A61C 8/00*    (2006.01)
*A61C 3/02*    (2006.01)

(52) U.S. Cl.
CPC .............. *A61C 8/0089* (2013.01); *A61C 3/02* (2013.01)

(58) Field of Classification Search
CPC ......... A61C 8/0089; A61C 3/02; A61C 1/084; A61C 1/10; B23B 51/00; B23B 27/10; A61B 17/1635; A61B 17/1637; A61B 17/1695; A61B 10/025; A61B 17/320024; A61B 17/320708; A61B 2017/1653; A61B 2017/1651
See application file for complete search history.

(56) References Cited

U.S. PATENT DOCUMENTS

| | | | | |
|---|---|---|---|---|
| 3,842,632 A | * | 10/1974 | Nelson | B21K 5/02 72/70 |
| 4,021,920 A | * | 5/1977 | Kirschner | A61C 8/0089 433/165 |
| 5,261,818 A | * | 11/1993 | Shaw | A61C 3/02 433/165 |
| 5,330,480 A | * | 7/1994 | Meloul | A61B 17/1695 606/80 |

(Continued)

FOREIGN PATENT DOCUMENTS

| | | | | |
|---|---|---|---|---|
| CN | 113648083 A | * | 11/2021 | |
| DE | 102009029714 A1 | * | 12/2010 | ......... A61B 17/1635 |

(Continued)

*Primary Examiner* — Heidi M Eide
*Assistant Examiner* — Lina Faraj
(74) *Attorney, Agent, or Firm* — MOSER TABOADA (57) ABSTRACT

Provided herein is a drill for a dental implant, which includes a coupling part connected to a hand piece configured to provide a rotational force, a body part disposed below the coupling part and configured to transmit the rotational force downward, a cutting part including a plurality of cutting blades and a void section, the cutting blades disposed below the body part to cut an alveolar bone and form a hole therein and being spaced apart at a predetermined angle in a rotational direction, and the void section surrounded by the cutting blades along at least a portion of an inner circumference of the cutting blades, and a coolant passage configured to communicate with the void section by passing through the coupling part and the body part and configured to, while the alveolar bone is being cut, supply coolant to the void section so that the coolant is introduced to the cutting blades.

7 Claims, 7 Drawing Sheets

(56) References Cited

U.S. PATENT DOCUMENTS

| | | | | |
|---|---|---|---|---|
| 5,941,706 | A * | 8/1999 | Ura | A61C 3/02 |
| | | | | 433/165 |
| 6,106,292 | A * | 8/2000 | Hollander | A61C 8/0089 |
| | | | | 408/59 |
| 9,795,457 | B2 * | 10/2017 | Friedrichs | B23B 51/06 |
| 10,548,693 | B2 * | 2/2020 | Wang | A61B 17/1673 |
| 2003/0022132 | A1 * | 1/2003 | Jesch | A61C 8/0089 |
| | | | | 433/165 |
| 2006/0111724 | A1 * | 5/2006 | Yeung Wai Ping | |
| | | | | A61B 17/1635 |
| | | | | 606/80 |
| 2006/0127847 | A1 * | 6/2006 | Danger | B23B 51/02 |
| | | | | 433/165 |
| 2006/0210949 | A1 * | 9/2006 | Stoop | A61C 8/0089 |
| | | | | 433/165 |
| 2008/0085488 | A1 * | 4/2008 | Lazarof | A61C 8/0089 |
| | | | | 433/50 |
| 2009/0053674 | A1 * | 2/2009 | Danger | A61C 3/02 |
| | | | | 433/102 |
| 2013/0122456 | A1 * | 5/2013 | Takebayashi | A61C 8/0089 |
| | | | | 433/75 |
| 2014/0113245 | A1 * | 4/2014 | Heo | A61C 8/0089 |
| | | | | 433/75 |
| 2017/0027594 | A1 * | 2/2017 | Ujvari | A61B 17/1617 |
| 2019/0388131 | A1 * | 12/2019 | Mehl | A61B 17/7055 |
| 2020/0029978 | A1 * | 1/2020 | Boukhris | A61C 1/082 |
| 2022/0160371 | A1 * | 5/2022 | Huwais | A61B 17/1644 |

FOREIGN PATENT DOCUMENTS

| | | | |
|---|---|---|---|
| DE | 202011002653 U1 * | 6/2011 | A61B 17/1673 |
| KR | 102270227 B1 * | 6/2021 | |
| WO | WO-2013042874 A1 * | 3/2013 | A61C 3/02 |

* cited by examiner

DRILL FOR DENTAL IMPLANT

CROSS-REFERENCE TO RELATED APPLICATION

This application claims priority to and the benefit of Korean Patent Application No. 10-2018-0046831, filed on Apr. 23, 2018, the disclosure of which is incorporated herein by reference in its entirety.

BACKGROUND

Field of the Invention

The present invention relates to a drill for a dental implant, and more particularly, to a drill for a dental implant capable of minimizing frictional heat caused during a drilling process in which a hole is formed due to cutting an alveolar bone and capable of smoothly introducing coolant, which minimizes the frictional heat, to a portion between the drill and the alveolar bone at a low pressure.

Discussion of Related Art

Generally, an implant refers to a replacement capable of being substituted for a human tissue when an original human tissue is damaged but, in dentistry, refers to implanting an artificial tooth. That is, placing an implant is an operation in which a fixture formed of a material such as titanium that is not rejected by the human body is implanted in an alveolar bone from which a tooth is lost so that the fixture substitutes for a lost tooth root and an artificial tooth is fixed to the fixture to restore functions of the lost tooth.

Although peripheral teeth and bone are damaged with time in the case of a general prosthesis or denture, an implant may prevent damage to peripheral dental tissues and may be stably used because there is no secondary cause of dental caries. Also, because an implant has the same structure as that of a natural tooth, the implant does not cause gum pain and foreign body sensation and thus may be semi-permanently used when managed well.

In the case of dental implant treatment based on osseointegration, when drilling a hole for inserting a fixture, which is an artificial tooth root, in an alveolar bone using a drill for a dental implant, excessive frictional heat occurs between the alveolar bone being cut around the hole and the drill. Such frictional heat causes loss of osseointegration as well as bacterial infection and excessive load, and thus the dental implant treatment cannot be performed stably.

For reduction of frictional heat, in the related art, coolant is supplied via an inner side of a drill through a small hole provided in the vicinity of a cutting blade located at a distal end of the drill in a drilling process. Although the coolant is supposed to be supplied to a space between the cutting blade and an alveolar bone where frictional heat is concentrated, in reality, pieces of bone or the like cut during the drilling process scatter and block the coolant hole. Accordingly, the coolant is not smoothly supplied. In order to solve such a problem, when a pressure at which the coolant is supplied is increased, the coolant scatters in the oral cavity excessively during the drilling process. Consequently, it becomes difficult to visually inspect the drilling process, and an unexpected operational failure occurs in the drilling which requires an accurate bore depth.

SUMMARY OF THE INVENTION

The present invention is directed to providing a drill for a dental implant capable of minimizing frictional heat caused during a drilling process in which a hole is formed due to cutting an alveolar bone and capable of smoothly introducing coolant, which minimizes the frictional heat, to a portion between the drill and the alveolar bone at a low pressure.

Objectives of the present invention are not limited to the above-mentioned objective, and other unmentioned objectives should be clearly understood by those of ordinary skill in the art from the description below.

According to an aspect of the present invention for achieving the above objective, a drill for a dental implant includes a coupling part connected to a hand piece configured to provide a rotational force, a body part disposed below the coupling part and configured to transmit the rotational force downward, a cutting part including a plurality of cutting blades and a void section, the cutting blades being disposed below the body part in order to cut an alveolar bone and form a hole therein and being spaced apart at a predetermined angle in a rotational direction, and the void section being surrounded by the cutting blades along at least a portion of an inner circumference of the cutting blades, and a coolant passage configured to communicate with the void section by passing through the coupling part and the body part and configured to, while the alveolar bone is being cut, supply coolant to the void section so that the coolant is introduced to the cutting blades.

In another embodiment, the void section may have a cross-sectional area larger than that of the coolant passage and be disposed to be surrounded from an upper side of the cutting blades adjacent to the body part to a predetermined position of the cutting blades, and an inner side of the cutting blades disposed below the void section may be integrally formed with the cutting blades without a void.

In still another embodiment, the cutting part may further include a concave section disposed above the cutting blades, disposed to be adjacent to the body part, and having a form that is concave toward the body part, and the coolant passage may pass through an apex of the concave section.

In yet another embodiment, the cutting part may further include a curved section configured to connect an upper portion of a preceding cutting blade and an upper portion of a following cutting blade which are adjacent to each other when viewed in the rotational direction, and the curved section may be connected to the preceding cutting blade and the following cutting blade such that a curved surface of the curved section that is disposed at the upper portion of the preceding cutting blade has a gentler slope than a surface of the curved section that is disposed at the upper portion of the following cutting blade.

In yet another embodiment, the void section exposed between the preceding cutting blade and the following cutting blade, which are adjacent to each other in the rotational direction, may be exposed with a larger area toward the body part in a vicinity of the preceding cutting blade than in a vicinity of the following cutting blade.

In yet another embodiment, each of the cutting blades may include upper cutting blades adjacent to the body part and lower cutting blades disposed below the upper cutting blade, the void section may be disposed to be surrounded by the upper cutting blades along at least a portion of an inner circumference thereof, and a guide groove between the upper cutting blade and the lower cutting blade may be provided to guide the coolant in a direction opposite to the rotational direction while the alveolar bone is being cut.

In yet another embodiment, the cutting blade may be formed as a helix type, the void section may be disposed to be surrounded by the cutting blade adjacent to the body part along a portion of an inner circumference of the cutting blade, and the drill may further include a side surface section formed as a surface without a step between the cutting blades below the void section.

Other details of the embodiments are incorporated in the following detailed description and the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, exemplary embodiments of the present invention will be described in detail with reference to the accompanying drawings. However, the present invention is not limited to the embodiments described herein and may also be embodied in other forms. The embodiments introduced herein are rather provided to make the content disclosed herein thorough and complete and to sufficiently convey the idea of the present invention to those of ordinary skill in the art. The same reference numerals refer to the same elements throughout. Meanwhile, the terms used herein are for describing the embodiments and are not intended to limit the present invention. A singular expression includes a plural expression unless particularly mentioned otherwise in the context. The terms "comprises", "includes" and/or "comprising", "including" used herein do not preclude the existence of or the possibility of adding one or more features, numbers, steps, operations, elements, parts, or combinations thereof other than those mentioned in advance.

Hereinafter, a drill for a dental implant according to an embodiment of the present invention will be described in detail with reference to FIGS. 1 to 4.

Figure 1:
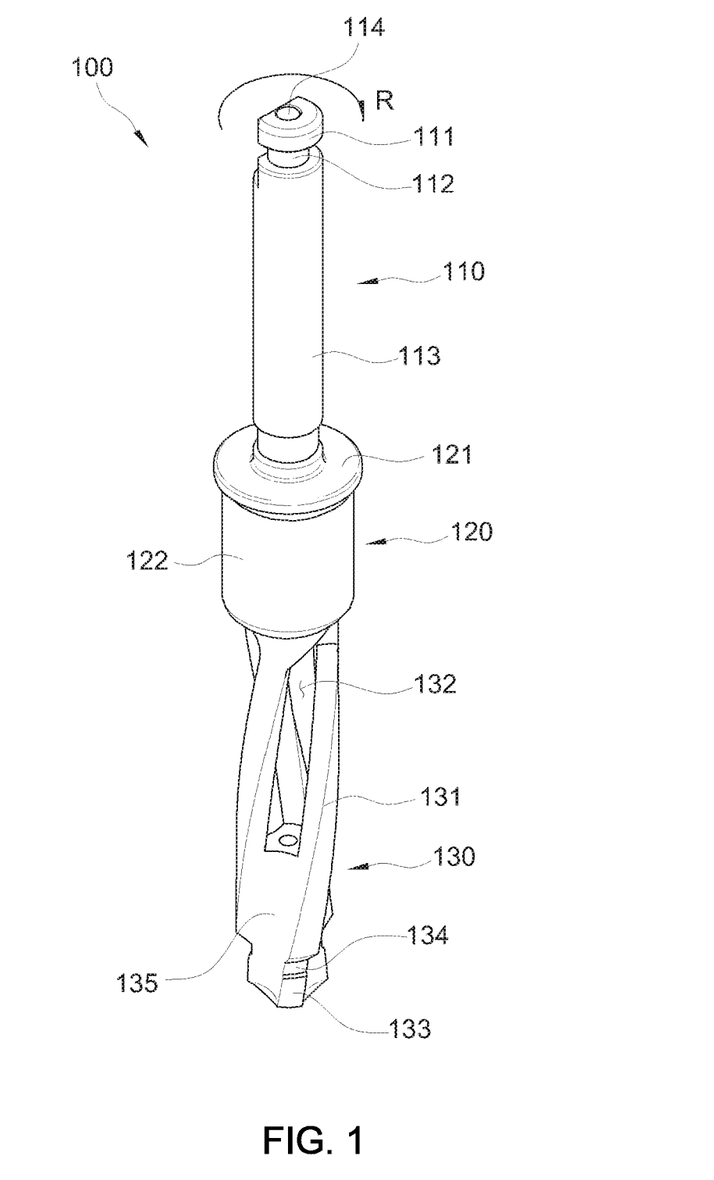
FIG. 1 is a top perspective view of a drill for a dental implant according to an embodiment of the present invention.
Figure 2:
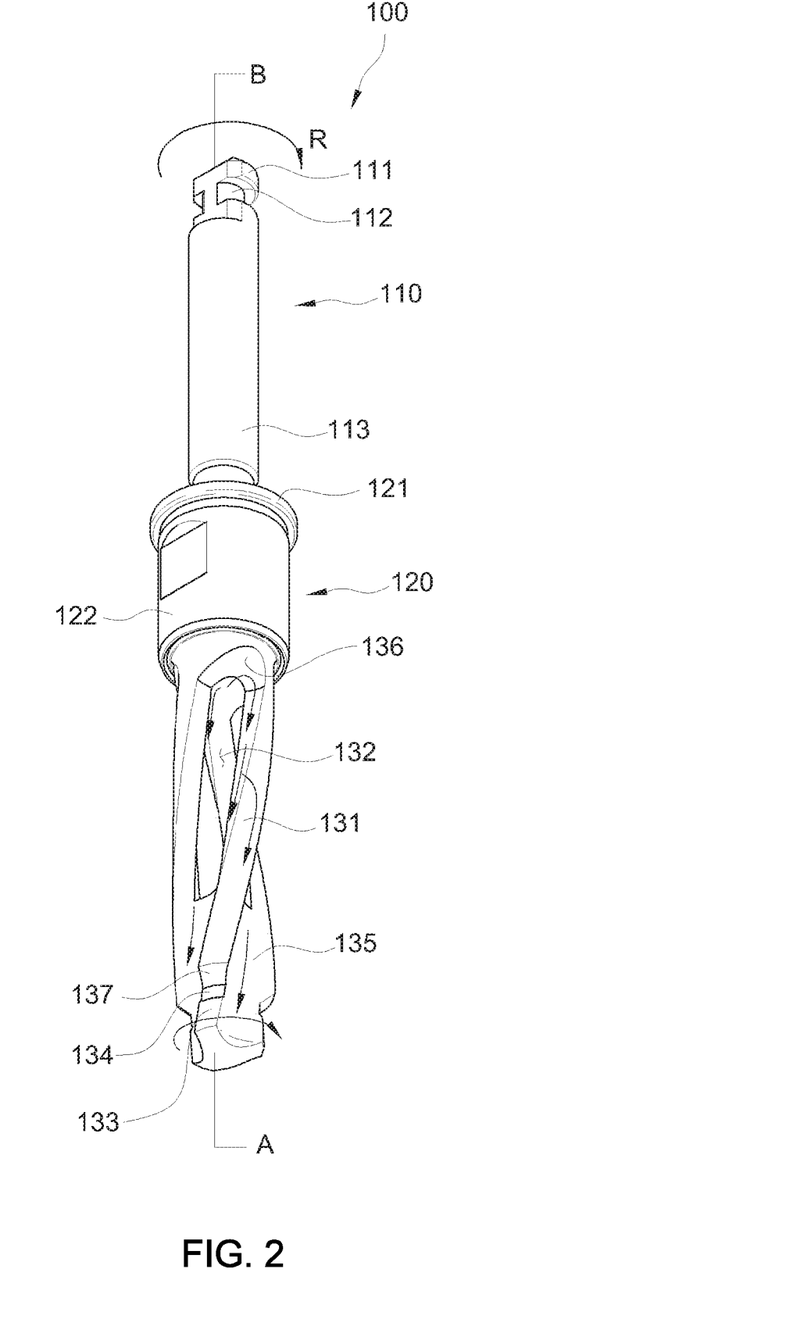
FIG. 2 is a bottom perspective view of the drill for a dental implant according to an embodiment of the present invention.
Figure 3:
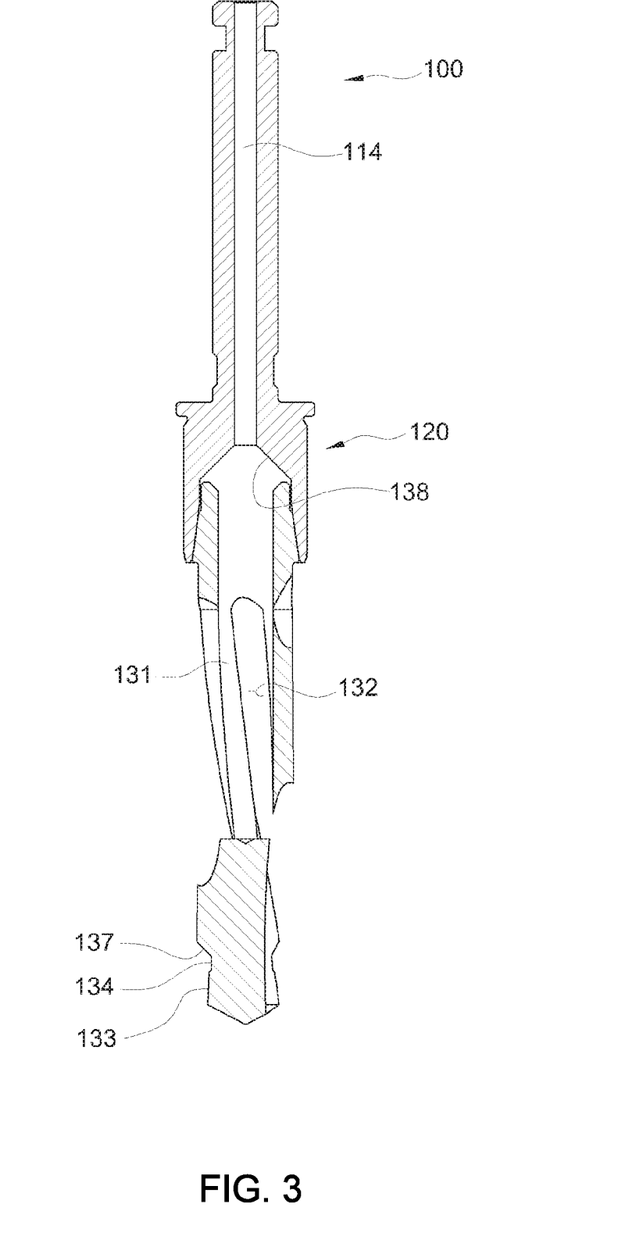
FIG. 3 is a cross-sectional view taken along line A-B in FIG. 2.

FIG. 1 is a top perspective view of a drill for a dental implant according to an embodiment of the present invention, FIG. 2 is a bottom perspective view of the drill for a dental implant according to an embodiment of the present invention, and FIG. 3 is a cross-sectional view taken along line A-B in FIG. 2.

A drill 100 for a dental implant according to an embodiment of the present invention includes a coupling part 110, a body part 120, a cutting part 130, and a coolant passage 114 passing through the coupling part 110 and the body part 120. Specifically, the drill 100 for a dental implant is used in a drilling process in which a hole for placement of a fixture is formed and is used in order to remove an alveolar bone 143 at a position at which an implant is to be placed in an oral cavity. In the drill 100 for a dental implant illustrated in FIGS. 1 to 3, cutting blades 131 and 133 of the cutting part 130 are formed as a helix type. The helical drill has excellent cutting force and force in the straight direction during hole formation.

Figure 5:
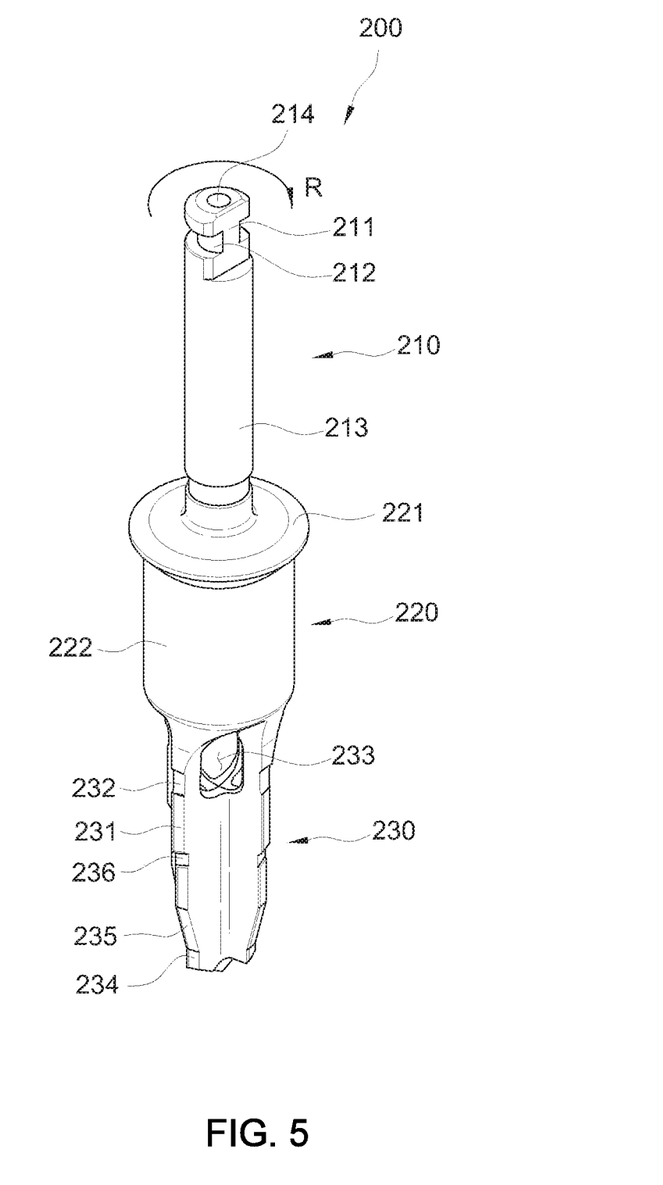
FIG. 5 is a top perspective view of a drill for a dental implant according to another embodiment of the present invention.
Figure 6:
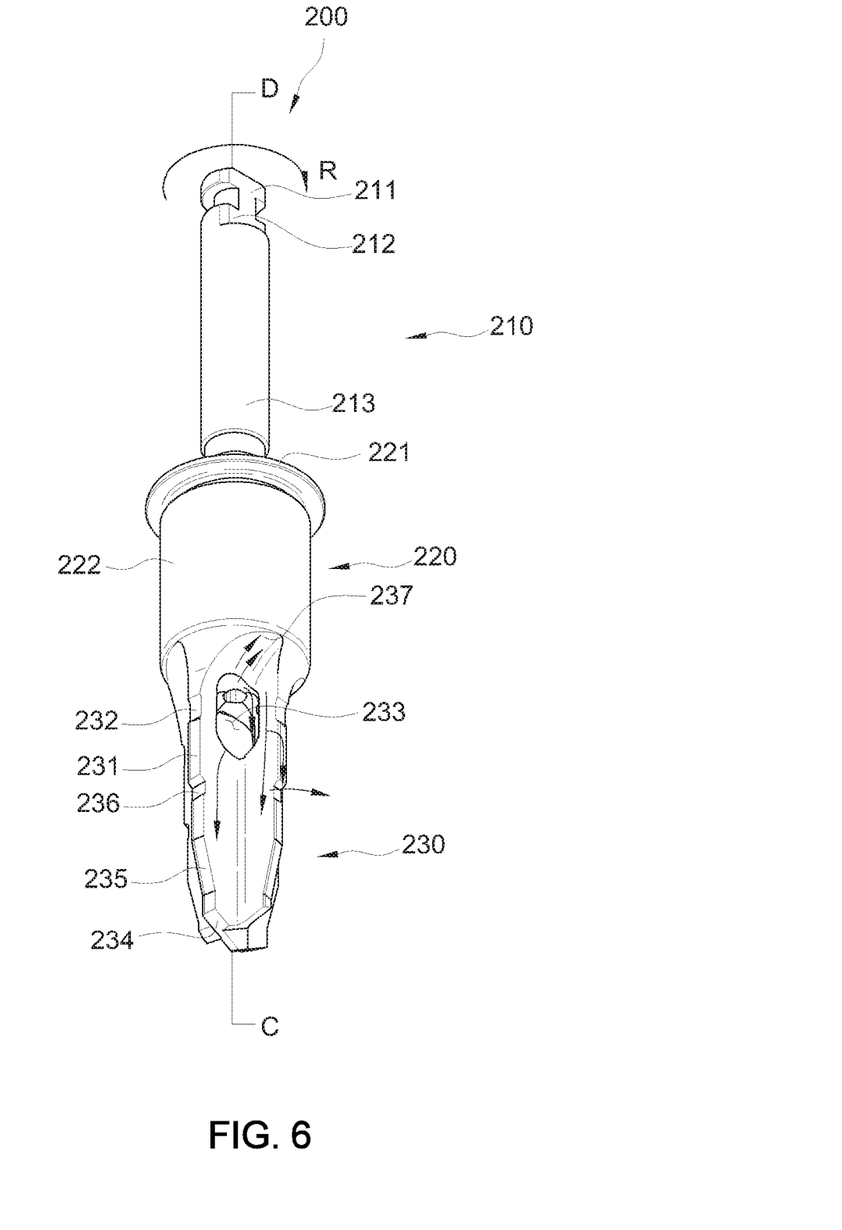
FIG. 6 is a bottom perspective view of the drill for a dental implant according to another embodiment of the present invention.
Figure 7:
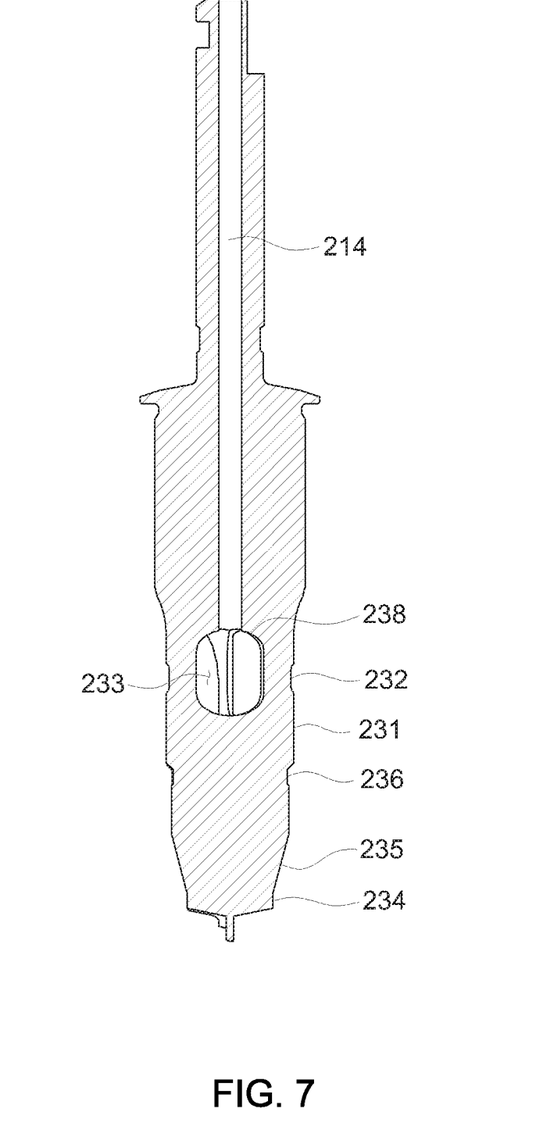
FIG. 7 is a cross-sectional view taken along line C-D in FIG. 6.

In the present embodiment, the coupling part 110, the body part 120, and the cutting part 130 are separately provided and coupled for convenience of a task of processing the coolant passage 114 and a task of replacing the cutting part 130 when the cutting part 130 is damaged. In this case, as illustrated in FIG. 3, the cutting part 130 may be joined to an inner side of the body part 120 by welding or the like. On the contrary, as illustrated in FIGS. 5 to 7, in a drill 100 for a dental implant according to another embodiment of the present invention, a coupling part 110, a body part 120, and a cutting part 130 may be integrally formed by cutting or electric-discharge machining.

Meanwhile, referring to FIGS. 1 and 2, the coupling part 110 has a mounting part 111 coupled to a dental hand piece (not illustrated) at an upper end of the mounting part 111. Here, the dental hand piece is a hand drill device used in order to provide a rotational force to the drill 100 for a dental implant, and a connection part coupled to the coupling part 110 is provided at one side of the dental hand piece.

In this case, the connection part may transmit a rotational force to the mounting part 111, and the mounting part 111 may be provided as a D-cut shape and integrally rotate with the connection part. Also, a locking groove 112 may be formed at a lower side of the mounting part 111, and thus the coupling part 110 may be firmly locked and fixed to the connection part without being deviated therefrom.

In addition, the coupling part 110 may connect the dental hand piece and the body part 120 and transmit the rotational force transmitted to the mounting part 111 to the body part 120. The coupling part 110 may be formed irrespective of a diameter of the body part 120 or the cutting part 130, but it is desirable that the coupling part 110 have a diameter smaller than that of the body part 120.

In this case, the coupling part 110 may be provided as a cylindrical shape. Consequently, the coupling part 110 may firmly support the body part 120 and the cutting part 130 during high-speed rotation. Also, because the coupling part 110 prevents damage due to rotation such as bending or twisting, durability of the drill 100 can be improved, and a decrease in drilling precision due to vibration caused by damage due to rotation can be prevented.

Figure 4:
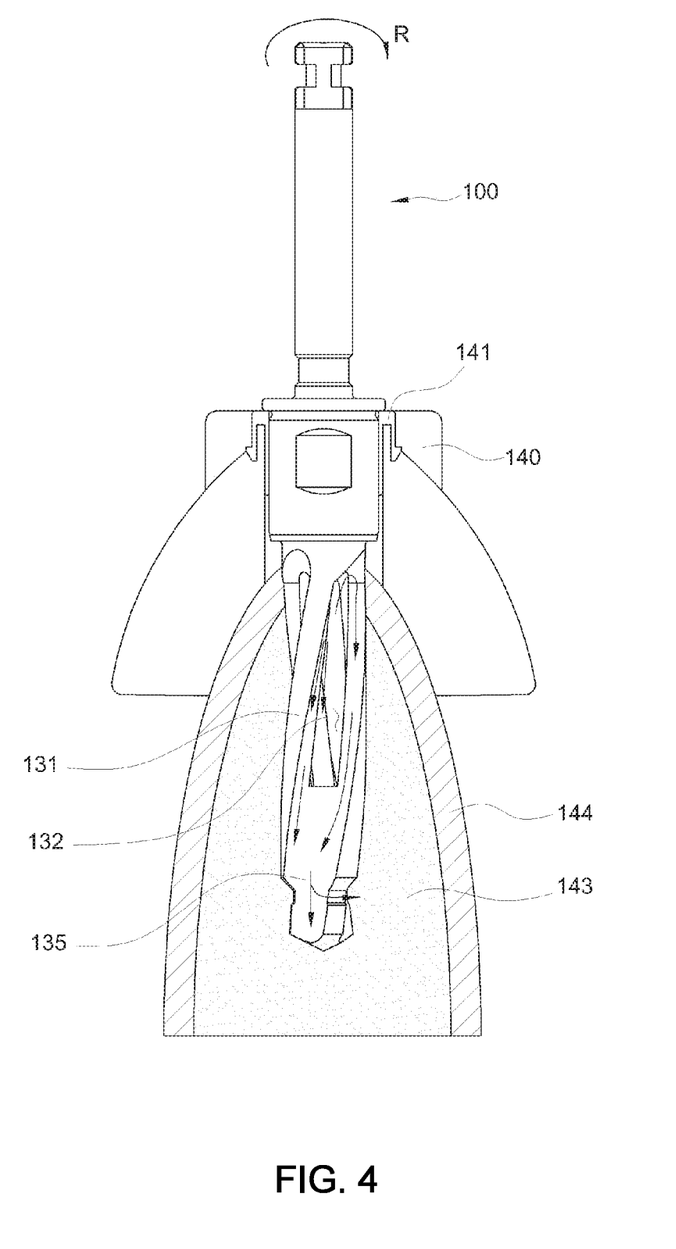
FIG. 4 is a view for describing an operation of the drill for a dental implant according to an embodiment of the present invention.

The body part 120 is connected to a lower side of the coupling part 110 and integrally rotates therewith in order to transmit a rotational force of the dental hand piece downward. Here, a fixing part 121 may be provided at an upper side of a body section 122 and connects to a column part 113, and the fixing part 121 may be formed to have a diameter larger than that of the body part 120. In this case, the drill 100 for a dental implant may be used by being inserted into a guide hole formed in a surgical guide 140, which is illustrated in FIG. 4, to guide accurate position and direction for a drilling task. In certain situations, the drill 100 for a dental implant may be disposed so that the fixing part 121 is supported by the guide hole.

The cutting part 130 is disposed below the body part 120 to cut the alveolar bone 143 and form a hole therein, includes a plurality of cutting blades 131 and 133 which are spaced apart at a predetermined angle in the rotational direction R (clockwise in the drawings) of the drill 100. The cutting part 130 has a void section 132 surrounded by the cutting blades 131 and 133 along at least a portion of an inner circumference of the cutting blades 131 and 133. Also, the coolant passage 114 communicates with the void section 132 and, when the alveolar bone 143 is being cut, supplies coolant to the void section 132 so that the coolant is introduced to the cutting blades 131 and 133. The coolant may be a saline solution or the like.

The void section 132 has a cross-sectional area larger than that of the coolant passage 114 and is disposed to be surrounded from an upper side of the cutting blades 131 and 133 adjacent to the body part 120 to a predetermined position of the cutting blades 131 and 133. An inner side of the cutting blades 131 and 133 disposed below the void section 132 may be integrally formed with the cutting blades 131 and 133 without a void.

Specifically, each of the cutting blades 131 and 133 may include upper cutting blades 131 adjacent to a lower portion of the body part 120 and lower cutting blades 133 disposed below the upper cutting blades 131. In this case, the void section 132 is formed to have a cross-sectional area larger than that of the coolant passage 114 and is surrounded by at least a portion of an inner circumference of the upper cutting blades 131. Although the void section 132 is illustrated in FIGS. 1 and 2 as corresponding to some of the upper cutting blades 131, according to design specifications, the void section 132 may be manufactured to correspond to all of the upper cutting blades 131.

Because the void section 132 is formed to have a cross-sectional area larger than that of the coolant passage 114, the coolant introduced from the coolant passage 114 may be smoothly sprayed in a wide range. Also, although cut bone dust freely passes through the void section 132 during the drilling process, movement of the bone dust to the coolant passage 114 is fundamentally blocked by a rotational centrifugal force of drilling. Consequently, because the cut bone dust does not block the coolant passage 114, the coolant may be smoothly introduced along the cutting blades 131 and 133.

While the alveolar bone 143 is being cut, a larger amount of bone dust is generated in the vicinity of the lower cutting blades 133, which initially come in contact with the alveolar bone 143, than in the vicinity of the upper cutting blades 131, and thus a large amount of bone dust is accumulated at the lower cutting blades 133 and the upper cutting blades 131 in the vicinity thereof. Because the void section 132 is located closer to the upper cutting blades 131 than to the cutting blades 133 where a large amount of bone dust is accumulated, a relatively small amount of bone dust is accumulated in the void section 132, and thus blockage of the coolant passage 114 can be suppressed.

In addition, in order to secure rigidities of the lower cutting blades 133, which initially come into contact with the alveolar bone 143 while the alveolar bone 143 is being cut, and the upper cutting blades 131 in the vicinity of the lower cutting blades 133, an inner space between the lower cutting blades 133 and an inner space of the upper cutting blades 131 up to a predetermined position may extend to corresponding lower and upper cutting blades 133 and 131 and be integrally formed therewith without a void.

Referring to FIG. 3, the cutting part 130 may further include a concave section 138 disposed above the upper cutting blades 131, disposed to be adjacent to the body part 120, and having a form that is concave toward the body part 120. The coolant passage 114 may pass through an apex of the concave section 138 and communicate with the void section 132.

The coolant passage 114 is located at the apex of the concave section 138 so that the coolant passage 114 is further spaced apart from the cutting blades 131 and 133 where a large amount of bone dust is generated and accumulated. In this way, blockage of the coolant passage 114 due to the cut bone dust can be prevented more effectively.

Because the coolant passage 114 is not blocked by the cut bone dust due to the position of the coolant passage 114 and the forms and positions of the concave section 138 and the void section 132 according to the present invention, the coolant can be smoothly introduced to a portion between the cutting blades 131 and 133 and the alveolar bone 143 at a low pressure. Consequently, frictional heat caused during a drilling process in which a hole is formed due to cutting the alveolar bone 143 can be minimized.

As illustrated in FIG. 2, the cutting part 130 may further include a curved section 136 configured to connect an upper portion of a preceding upper cutting blade 131 and an upper portion of a following upper cutting blade 131 which are adjacent to each other when viewed in the rotational direction R. In this case, the curved section 136 may be connected to the preceding upper cutting blade 131 and the following upper cutting blade 131 such that a curved surface of the curved section 136 that is disposed at the upper portion of the preceding upper cutting blade 131 has a gentler slope than a surface of the curved section 136 that is disposed at the upper portion of the following upper cutting blade 131.

Due to the above-described slope form, the curved section 136 is formed to match a trajectory of coolant generated due to a centrifugal force generated during rotation in the rotational direction R. Therefore, the coolant that has passed through the coolant passage 114 and the concave section 138 may be introduced from the top of the upper cutting blades 131 as a coolant flow passage indicated by an arrow in FIG. 2. Accordingly, the cooling range can be maximized.

Meanwhile, the upper cutting blades 131 may be provided in plural so that a contact area with the alveolar bone 143 is decreased, and the upper cutting blades 131 may be spaced apart from each other at a predetermined angle in the rotational direction R of the drill 100. Although it is desirable that three upper cutting blades 131 be provided, the drill 100 may be manufactured to include various other numbers of upper cutting blades 131 according to an operational environment, design specifications, and the like.

Because the plurality of upper cutting blades 131 are spaced apart from each other, a contact area between the upper cutting blades 131 and the alveolar bone 143 decreases. Therefore, generation of excessive frictional heat due to drilling can be minimized.

Accordingly, because necrosis of the gum 144 and the alveolar bone 143 due to thermal damage and excessive heat is minimized while the alveolar bone 143 is being cut by rotation of the upper cutting blades 131, safety of the drill 100 can be significantly improved. Furthermore, because excessive frictional heat is minimized, which leads to decreases in a pressure at which coolant, such as a saline solution, is supplied, an amount by which the coolant is supplied, and the number of instances of supplying the coolant, convenience of performing dental implant treatment can be significantly improved.

Outer circumferential surfaces of the upper cutting blades 131 may be formed to be round to correspond to an outer circumference of a hole to be formed in the alveolar bone 143. Although the outer circumferential surface of the upper cutting blade 131 may also be formed to be flat or polygonal, it is desirable that the outer circumferential surface be formed to be round so that a fixture is stably placed in the hole.

In this case, a virtual diameter along the outer circumference of the upper cutting blades 131 may be set to correspond to a diameter of the hole, and the upper cutting blades 131 may have a diameter smaller than an inner circumference of a guide hole of the surgical guide 140 or a sleeve 141 so that the upper cutting blades 131 pass through the inner circumference of the guide hole.

The upper cutting blade 131 extends downward by a predetermined length. A length of the upper cutting blade 131 may be set so that a length between the upper cutting blade 131 and distal ends of the lower cutting blade 133 correspond to a length of a fixture to be placed.

In addition, it is desirable that the upper cutting blade 131 extend downward perpendicularly. However, according to circumstances, the upper cutting blade 131 may also extend radially inward to become narrower downward.

It is desirable that an outer portion of the lower cutting blade 133 be connected to the upper cutting blade 131 so that the lower cutting blade 133 cuts the alveolar bone 143, which is at the position at which a fixture will be placed, and forms a hole in the alveolar bone 143. In this case, the lower cutting blade 133 may include a distal end cutting blade integrally extending from an end of the upper cutting blade 131.

Because the lower cutting blades 133 integrally extend from the upper cutting blades 131, the lower cutting blades 133 may be spaced apart at the same width as that at which the upper cutting blades 131 are spaced apart from each other. Also, because the lower cutting blade 133 is connected to the other end of each upper cutting blade 131, it is desirable that three lower cutting blades 133 be provided. According to a treatment situation, design conditions, and the like, the number of lower cutting blades 133 and the upper cutting blades 131 may be any plural number that is two or greater, and the numbers of the lower cutting blades 133 and the upper cutting blades 131 may also be different from each other.

Due to a structure in which the lower cutting blades 133 are spaced apart from each other and the upper cutting blades 131 are spaced apart from each other, a frictional area is minimized, and thus generation of excessive frictional heat is minimized. In this way, safety of the drill 100 can be improved.

It is desirable that the lower cutting blades 133 be disposed radially about a rotation axis. In this case, inner ends of the lower cutting blades 133 may extend inward and be connected to each other in an integrated shape. Here, a diameter formed by the lower cutting blades 133 may become gradually narrower toward a distal end of each lower cutting blade 133, and a center-of-rotation point may be formed to be sharp.

To prevent an occurrence of an error in a hole formation position while an initial position for drilling is set, the lower cutting blade 133 may come into point contact with the alveolar bone 143 and may stably enter the alveolar bone 143 due to the rotational force of the dental hand piece.

The lower cutting blades 133 may have a shape that gradually becomes narrower radially inward. Also, outer circumferential surfaces of the lower cutting blades 133 may be formed to be round corresponding to an outer circumference of an initial hole so that the cut alveolar bone 143 does not remain in a gap between the lower cutting blade 131 and the hole.

Meanwhile, the cutting part 130 may further include a side surface section 135 formed as a surface without a step between the upper cutting blades 131 or lower cutting blades 133 below the void section 132. As illustrated in FIG. 2, the side surface section 135 contributes to smoothly supplying coolant to the cutting blades 131 and 133, to which heat generation is concentrated, without any hindrance during the drilling process.

In addition, the cutting part 130 may further include a step section 137 formed at an outer surface of a connection portion of the upper cutting blades 131 and the lower cutting blades 133.

Here, an outer diameter along an outer circumference of the lower cutting blades 133 may be formed to be smaller than the outer diameter along the outer circumference of the upper cutting blades 131, and, as the diameter formed by the lower cutting blades 133 becomes smaller, a rotational force may be increased, and initial formation of the hole in the alveolar bone 143 may be facilitated. That is, the step section 137 may be provided to obliquely connect the outer surfaces of the upper and lower cutting blades 131 and 133 which are formed at different diameters.

In this case, as the alveolar bone 143 is being cut by the lower cutting blades 133, and the lower cutting blades 133 enter a fine hole, an initial hole having a diameter smaller than that of a hole in which a fixture is to be placed may be formed. Also, as the drilling task continues, the upper cutting blades 131 may enter the initial hole after the lower cutting blades 133 and may expand corresponding to the hole in which a fixture is to be placed.

Here, the step section 137 may be formed to be inclined outward from the lower cutting blades 133 toward the upper cutting blades 131 so that the initial hole gradually expands. Consequently, because an excessive load due to changes in the diameters of the cutting blades 131 and 133 is prevented, and wear of the cutting blades 131 and 133 due to friction with the alveolar bone 143 is minimized, the durability of the drill 100 can be improved.

Referring back to FIG. 2, the cutting part 130 includes a guide groove 134 disposed between each upper cutting blade 131 and the lower cutting blade 133 therebelow. The guide groove 134 may be formed to be inclined upward in a direction opposite to the rotational direction R to guide coolant in the direction opposite to the rotational direction R while the alveolar bone 143 is being cut. Accordingly, the coolant may be evenly distributed to the lower cutting blades 133 to which heat generation is concentrated. Also, because the drill 100 rotates while the guide groove 134 causes the cut bone dust to remain at the outer circumference of the upper cutting blades 131, the guide groove 134 contributes to preventing accumulation of bone dust in the void section 132.

Hereinafter, an operation and a coolant flow of the drill for a dental implant according to an embodiment of the present invention will be described with reference to FIGS. 1 to 4.

FIG. 4 is a view for describing an operation of the drill for a dental implant according to an embodiment of the present invention.

During a dental implant treatment process, because it is difficult to accurately identify the position and direction in which drilling should be performed when forming a hole in which a fixture is to be placed, an auxiliary tool referred to as "surgical guide 140" may be used.

Here, the surgical guide 140 is formed to have a profile of an inside of an oral cavity according to a dental implant treatment plan based on oral cavity information including data on the gum 144, teeth, alveolar bone 143 and the like of a patient and is inserted into the oral cavity to surround and fix teeth and gums.

An anchor hole (not illustrated) may be provided in a side portion of the surgical guide 140, an anchor pin (not illustrated) may be inserted into the anchor hole, and as the anchor pin is inserted to the gum 144 and the alveolar bone 143 of the patient and then fixed, the surgical guide 140 may be fixed to the inside of the oral cavity.

Accordingly, while the surgical guide 140 is fixed, the surgical guide 140 may stably guide any task required for dental implant treatment such as a drilling task. Also, a guide hole may be formed in the surgical guide 140 corresponding to the number of dental implants to be placed according to positions where fixtures will be placed.

Of course, the guide hole may be directly formed in the surgical guide 140, but the guide hole may also be formed through a sleeve 141 which is formed of a metal material and additionally coupled to the surgical guide 140 to stably and rotatably support the drill 100 by decreasing a frictional force and preventing deformation of the drill 100 during rotation of the drill 100. The sleeve 141 is detachable from the surgical guide 140, and, for a strong coupling force during rotation of the drill 100, the sleeve 141 may have a fixing protrusion having an elastic force formed at an outer circumference of a cylindrical shape having a hollow.

In this case, the body part 120 may have an outer diameter corresponding to an inner circumference of the guide hole to be inserted into the guide hole and be rotatably supported thereby. Also, sleeves 141 having various outer diameters may be provided according to an outer diameter of the body part 120 to be inserted, and the sleeve 141 suitable for the drill 100 selected by an operator may be mounted on the surgical guide 140. Furthermore, a lower surface of the fixing part 121 may be flat while a diameter thereof is larger than that of the guide hole.

Accordingly, when the body part 120 is inserted into the guide hole and the cutting blades 131 and 133 are disposed at teeth and gums of a patient via the inner side of the guide hole, the lower surface of the fixing part 121 may be seated on the top edge of the guide hole and then restrained.

The drill 100 for a dental implant, the surgical guide 140, and the sleeve 141 described above with reference to FIGS. 1 to 4 may constitute a drill set for a dental implant that is used while forming a hole in the alveolar bone 143 and may be provided to an operator as a set.

When an operator forms a hole for a fixture in the alveolar bone 143 by using the drill set for a dental implant, the operator places the surgical guide 140 at a position where drilling will be performed, mounts the sleeve 141 on the corresponding position, and then causes the drill 100 for a dental implant, which is coupled to a dental hand piece, to pass through the guide hole of the sleeve 141. Next, the operator rotates the drill 100, and, in this process, coolant such as a saline solution which is supplied from the dental hand piece is supplied to the void section 132 through the coolant passage 114. In this case, the operator locates a suction (not illustrated) in the oral cavity and suctions scattered bone dust and coolant which has been introduced into the drill 100 and has leaked to the oral cavity via the surgical guide 140 during the drilling process.

As coolant flow passages indicated by arrows in FIGS. 2 and 4, the coolant flows to the curved section 136 along the concave section 138 due to a rotational centrifugal force. Because the curved section 136 is formed such that the curved surface of the curved section 136 that is disposed at the upper portion of the preceding upper cutting blade 131 has a gentler slope than a surface of the curved section 136 that is disposed at the upper portion of the following upper cutting blade 131, the coolant is introduced from the top of the upper cutting blades 131 to maximize the cooling range.

Further, when a flow rate of the coolant is set to be high, the coolant is introduced toward the lower cutting blades 133 while filling most of the void section 132.

That is, the coolant flows to cover all of both side surfaces, namely, outer and inner surfaces of the upper cutting blades 131 and flows to all surfaces of the lower cutting blades 133 and the side surface section 135 between the lower cutting blades 133. Accordingly, the frictional heat caused during the drilling process in which a hole is formed due to cutting the alveolar bone 143 can be minimized.

Further, because the void section 132 is formed to have a cross-sectional area larger than that of the coolant passage 114, the coolant introduced from the coolant passage 114 can be smoothly sprayed in a wide range. Also, although cut bone dust freely passes through the void section 132 during the drilling process, movement of the bone dust to the coolant passage 114 is fundamentally blocked by a rotational centrifugal force of the drilling. Consequently, because the cut bone dust does not block the coolant passage 114, the coolant may be smoothly introduced along the cutting blades 131 and 133.

While the alveolar bone 143 is being cut, a larger amount of cut bone dust is generated in the vicinity of the lower cutting blades 133, which initially come in contact with the alveolar bone 143, than in the vicinity of the upper cutting blades 131, and thus a large amount of bone dust is accumulated at the lower cutting blades 133 and the upper cutting blades 131 in the vicinity thereof. Because the void section 132 is located closer to the upper cutting blades 131 than to the cutting blades 131 and 133 where a large amount of bone dust is accumulated, a relatively small amount of bone dust is accumulated in the void section 132, and thus blockage of the coolant passage 114 can be suppressed.

Consequently, because the coolant passage 114 is not blocked by the cut bone dust due to the position of the coolant passage 114 and the forms and positions of the concave section 138, the curved section 136, and the void section 132 according to the present embodiment, the coolant can be smoothly introduced to a portion between the cutting blades 131 and 133 and the alveolar bone 143 at a low pressure.

Hereinafter, a drill for a dental implant according to another embodiment of the present invention will be described with reference to FIGS. 5 to 7.

FIG. 5 is a top perspective view of a drill for a dental implant according to another embodiment of the present invention, FIG. 6 is a bottom perspective view of the drill for a dental implant according to another embodiment of the present invention, and FIG. 7 is a cross-sectional view taken along line C-D in FIG. 6.

A drill 200 for a dental implant according to FIGS. 5 to 7 is a straight type in which cutting blades 231, 233, and 234 of a cutting part 230 protrude perpendicularly. The straight drill is inferior to the helical drill in terms of the force in the straight direction during hole formation but is superior thereto in terms of hole processing accuracy.

In the description of the present embodiment, description of members, functions, effects, and the like which are substantially the same as the drill 100 according to the above embodiment illustrated in FIGS. 1 to 4 will be omitted, and differences from the drill 100 according to the embodiment illustrated in FIGS. 1 to 4 will be mainly described.

The drill 200 for a dental implant according to FIGS. 5 to 7 also includes a coupling part 210, a body part 220, a cutting part 230, and a coolant passage 214 passing through the coupling part 210 and the body part 220. The coupling part 210 may include a mounting part 211, a locking groove 212, and a column part 213, and the body part 220 may include a fixing part 221 and a body section 222. The above-mentioned members are substantially the same as the members having identical names which have been described above with reference to FIGS. 1 to 4.

From the vicinity of the body part 220 toward a distal end of the drill 200, the cutting part 230 has a plurality of cutting blades 231, 234, and 235 disposed in that order which are spaced apart at a predetermined angle in a rotational direction R (clockwise in the drawings) of the drill 200 and has a void section 233 surrounded by upper cutting blades 231 along at least a portion of an inner circumference of the upper cutting blade 231. Also, the coolant passage 214 communicates with the void section 233 and, while the alveolar bone 143 (see FIG. 4) is being cut, supplies coolant, e.g., a saline solution, to the void section 233 so that the coolant is introduced to the cutting blades 231, 234, and 235.

Specifically, each of the cutting blades 231, 234, and 235 may include the upper cutting blades 231, first lower cutting blades 235, and second lower cutting blades 234 in an order moving away from a distal end of the body part 220. In this case, the void section 233 is formed to have a cross-sectional area larger than that of the coolant passage 214 and is surrounded by at least a portion of an inner circumference of the upper cutting blades 231.

Referring to FIG. 7, the cutting part 230 may further include a concave section 238 disposed above the upper cutting blades 231, disposed to be adjacent to the body part 220, and having a form that is concave toward the body part 220. The coolant passage 214 may pass through an apex of the concave section 238 and communicate with the void section 233.

As illustrated in FIG. 6, the cutting part 230 may further include a curved section 237 configured to connect upper portions of a preceding upper cutting blade 231 and a following upper cutting blade 231 which are adjacent to each other when viewed in the rotational direction R. In this case, the curved section 237 may be connected to the preceding upper cutting blade 231 and the following upper cutting blade 231 such that a curved surface of the curved section 237 that is disposed at the upper portion of the preceding upper cutting blade 231 has a gentler slope than a surface of the curved section 237 that is disposed at the upper portion of the following upper cutting blade 231.

In addition, the void section 233 exposed between the preceding upper cutting blade 231 and the following upper cutting blade 231, which are adjacent to each other when viewed in the rotational direction R, may be exposed with a larger area toward the body part 220 in the vicinity of the preceding upper cutting blade 231 than in the vicinity of the following upper cutting blade 231.

Accordingly, due to the above-described shapes of the curved section 237 and the void section 233, the curved section 237 and the void section 233 are formed to match a trajectory of coolant generated due to a centrifugal force generated during rotation in the rotational direction R. Therefore, as a coolant flow passage indicated by an arrow in FIG. 6, the coolant that has passed through the coolant passage 214 and the concave section 238 may be introduced at a larger amount to the top of the upper cutting blades 231. Accordingly, the cooling range can be maximized.

Meanwhile, the upper cutting blades 231 may be provided in plural so that a contact area with the alveolar bone 143 decreases and may be spaced apart from each other at a predetermined angle in the rotational direction R of the drill 200. In the case of the straight drill 200, although it is desirable that four upper cutting blades 231 be provided, the drill 200 may be manufactured to include various other numbers of upper cutting blades 231 according to an operational environment, design specifications, and the like.

The upper cutting blade 231 corresponding to the void section 233 may further include a recess 232. While the alveolar bone 143 is being cut, the recess 232 guides the coolant supplied through the void section 233 in a direction opposite to the rotational direction R, and the drill 200 rotates while the recess 232 causes the cut bone dust to remain at the outer circumference of the upper cutting blades 231. In this way, the recess 232 contributes to preventing accumulation of bone dust in the void section 233.

The first lower cutting blades 235 may be integrally connected with the upper cutting blades 231. The first lower cutting blades 235 may be formed to have a profile of the same outer diameter from a middle portion to the upper cutting blades 231 while being tapered so that a virtual outer diameter connecting outer sides of the first lower cutting blades 235 becomes gradually larger than a virtual outer diameter connecting outer sides of the second lower cutting blades 234 toward the upper cutting blades 231.

According to such a form, as the drilling task continues, the first lower cutting blades 235 may enter an initial hole after the second lower cutting blades 234 and may expand a diameter of a hole in which a fixture is to be placed without causing excessive load and stress.

The second lower cutting blades 234 may integrally extend from the first lower cutting blades 235 and may be manufactured to have a virtual outer diameter smaller than that of the first lower cutting blades 235.

Consequently, to prevent an occurrence of an error in a hole formation position while an initial position for drilling is set, the second lower cutting blade 234 may come into point contact with the alveolar bone 143 and may stably enter the alveolar bone 143 due to the rotational force of the dental hand piece.

The second lower cutting blades 234 may have a shape that gradually becomes narrower radially inward. Also, outer circumferential surfaces of the second lower cutting blades 234 may be formed to be round corresponding to an outer circumference of an initial hole so that the cut alveolar bone 143 does not remain in a gap between the second lower cutting blade 234 and the hole.

Meanwhile, the cutting part 230 may further include a step section (not denoted by a reference numeral) formed at an outer surface of a connection portion of the upper cutting blades 231 and the first lower cutting blades 235 that is similar to the step section 137 illustrated in FIGS. 1 to 4.

Here, an outer diameter along an outer circumference of the first lower cutting blades 235 may be formed to be smaller than the outer diameter along the outer circumference of the upper cutting blades 231, and, as the diameter formed by the first lower cutting blades 235 becomes smaller, a rotational force may be increased, and initial formation of the hole in the alveolar bone 143 may be facilitated. That is, the step section may be provided to obliquely connect the outer surfaces of the upper cutting blades 231 and the first lower cutting blades 235 which are formed at different diameters.

The step section may be formed to be inclined outward from the first lower cutting blades 235 toward the upper cutting blades 231 so that the initial hole gradually expands. Consequently, because an excessive load due to changes in the diameters of the cutting blades 231 and 235 is prevented, and wear of the cutting blades 231 and 235 due to friction with the alveolar bone 143 is minimized, the durability of the drill 200 can be improved.

Referring back to FIG. 6, the cutting part 230 includes a guide groove 236 disposed between each upper cutting blade 231 and the first lower cutting blade 235. The guide groove 236 may be formed to be inclined upward in a direction opposite to the rotational direction R to guide coolant in the direction opposite to the rotational direction R while the alveolar bone 143 is being cut and cause the cut bone dust to remain in the guide groove 236.

According to the present invention, frictional heat caused during a drilling process in which a hole is formed due to cutting an alveolar bone can be minimized, and coolant, which minimizes the frictional heat, can be smoothly introduced to a portion between the drill and the alveolar bone at a low pressure.

The present invention has been described above in detail with reference to exemplary embodiments, but one of ordinary skill in the art should understand that various modifications may be made to the embodiments within the scope not departing from the gist of the present invention. Therefore, the scope of the present invention should not be limitedly defined by the embodiments but should be defined by the claims below and all changes or modifications derived from their equivalents.

What is claimed is:

1. A drill for a dental implant, the drill comprising;
   a coupling part connected to a hand piece configured to provide a rotational force;
   a body part disposed below the coupling part and configured to transmit the rotational force downward;
   a cutting part including a plurality of cutting blades, a curved section that abuts the body part, a concave section, and a void section at least partially defined by an inner circumference of a sidewall of the cutting part and at least partially defined by the concave section below the curved section such that the concave section blends into the curved section, the cutting blades being disposed below the body part in order to cut an alveolar bone and form a hole therein and being spaced apart at a predetermined angle in a rotational direction, and the void section being surrounded by the cutting blades along at least a portion of an inner circumference of the cutting blades, and a coolant passage configured to communicate with the void section by passing through the coupling part and the body part and configured to, while the alveolar bone is being cut, supply coolant to the void section so that the coolant is introduced to the cutting blades; wherein the concave section is disposed above the cutting blades, disposed to be adjacent to the body part, and having a form that is concave toward the body part, wherein the coolant passage passes through an apex of the concave section.

2. The drill of claim 1, wherein the void section has a cross-sectional area larger than that of the coolant passage and is disposed to be surrounded from an upper side of the cutting blades adjacent to the body part to a predetermined position of the cutting blades, and an inner side of the cutting blades disposed below the void section is integrally formed with the cutting blades without a void.

3. The drill of claim 1, wherein the curved section is configured to connect an upper portion of a preceding cutting blade and an upper portion of a following cutting blade which are adjacent to each other when viewed in the rotational direction,
   wherein the curved section is connected to the preceding cutting blade and the following cutting blade such that a curved surface of the curved section that is disposed at the upper portion of the preceding cutting blade has a gentler slope than a surface of the curved section that is disposed at the upper portion of the following cutting blade.

4. The drill of claim 1, wherein the void section exposed between a preceding cutting blade and a following cutting blade, which are adjacent to each other in the rotational direction, is exposed with a larger area toward the body part in a vicinity of the preceding cutting blade than in a vicinity of the following cutting blade.

5. The drill of claim 1, wherein:
   each of the cutting blades includes upper cutting blades adjacent to the body part and lower cutting blades disposed below the upper cutting blade; and
   a guide groove between the upper cutting blade and the lower cutting blade is provided to guide the coolant in a direction opposite to the rotational direction while the alveolar bone is being cut.

6. The drill of claim 1, wherein:
   the cutting blade is formed as a helix type, and the void section is disposed to be surrounded by the cutting blade adjacent to the body part along a portion of an inner circumference of the cutting blade; and
   the drill further comprises a side surface section formed as a surface without a step between the cutting blades below the void section.

7. The drill of claim 1, wherein the curved section and the void section are formed to match a trajectory of coolant generated such that as coolant passes through the coolant passage and the concave section the coolant is introduced at a larger amount to a top of the cutting blades as opposed to a bottom of the cutting blades to maximize a cooling range to the cutting part.

* * * * *

UNITED STATES PATENT AND TRADEMARK OFFICE
CERTIFICATE OF CORRECTION

PATENT NO. : 12,036,090 B2  
APPLICATION NO. : 16/387907  
DATED : July 16, 2024  
INVENTOR(S) : Haeng Oh Kim et al.

Page 1 of 1

It is certified that error appears in the above-identified patent and that said Letters Patent is hereby corrected as shown below:

On the Title Page

Insert:  
--(30) Foreign Application Priority Data  
April 23, 2018 (KR) ...................... 10-2018-0046831--

Signed and Sealed this  
Thirty-first Day of December, 2024

Derrick Brent  
*Acting Director of the United States Patent and Trademark Office*